US005694937A

United States Patent [19]
Kamiyama

[11] Patent Number: 5,694,937
[45] Date of Patent: Dec. 9, 1997

[54] ULTRASOUND DIAGNOSTIC APPARATUS AND METHOD

[75] Inventor: Naohisa Kamiyama, Otawara, Japan

[73] Assignee: Kabushiki Kaisha Toshiba, Kawasaki, Japan

[21] Appl. No.: 593,886

[22] Filed: Jan. 30, 1996

[30] Foreign Application Priority Data

| Jan. 31, 1995 | [JP] | Japan | 7-013874 |
| Apr. 14, 1995 | [JP] | Japan | 7-089773 |
| Jun. 9, 1995 | [JP] | Japan | 7-143525 |

[51] Int. Cl.$^6$ ............................................. A61B 8/00
[52] U.S. Cl. ............................ 128/661.01; 128/662.02
[58] Field of Search ..................... 128/662.02, 660.05, 128/661.01

[56] References Cited

U.S. PATENT DOCUMENTS 5,255,683  10/1993  Monaghan ............... 128/662.02
5,410,516  4/1995  Uhlendorf et al. .

OTHER PUBLICATIONS

Christy K. Holland, et al., "In Vitro Detection of Cavitation Induced by a Diagnostic Ultrasound System" IEEE Transactions On Ultrasonics, Ferroelectrics, and Frequency Control, vol. 39, No. 1, Jan. 1992.

Primary Examiner—Marvin M. Lateef
Assistant Examiner—Derrick Fields
Attorney, Agent, or Firm—Oblon, Spivak, McClelland, Maier & Neustadt, P.C.

[57] ABSTRACT

According to an ultrasound diagnostic apparatus of the present invention, a cross section of an examining human body having bubbles implanted as ultrasonic shadowing agent is scanned by an ultrasound so as to obtain an echo signal. Image data is repeatedly generated based on the echo signal. Then, image data is displayed as a motion image. Power of the ultrasound to be transmitted is changed from first power to second power, which is stronger than first power. The ultrasound of first power breaks a first amount of bubbles. The ultrasound of second power, which is stronger than first power, breaks a second amount of bubbles, which is larger than the first amount of bubbles. Though the image generated by use of first power is unclear, the amount of breakage of bubbles can be extremely retrained. Since the image is used to examine the state of the bubble flow to the region of interest, unclearness can be allowed. When the bubbles are fully introduced to the region of interest, first power is changed to second power. Second power is stronger than first power. Therefore, the image obtained by second power is clearer than image obtained by first power, and is fit for a high accurate diagnosis of the state of the blood stream.

28 Claims, 10 Drawing Sheets

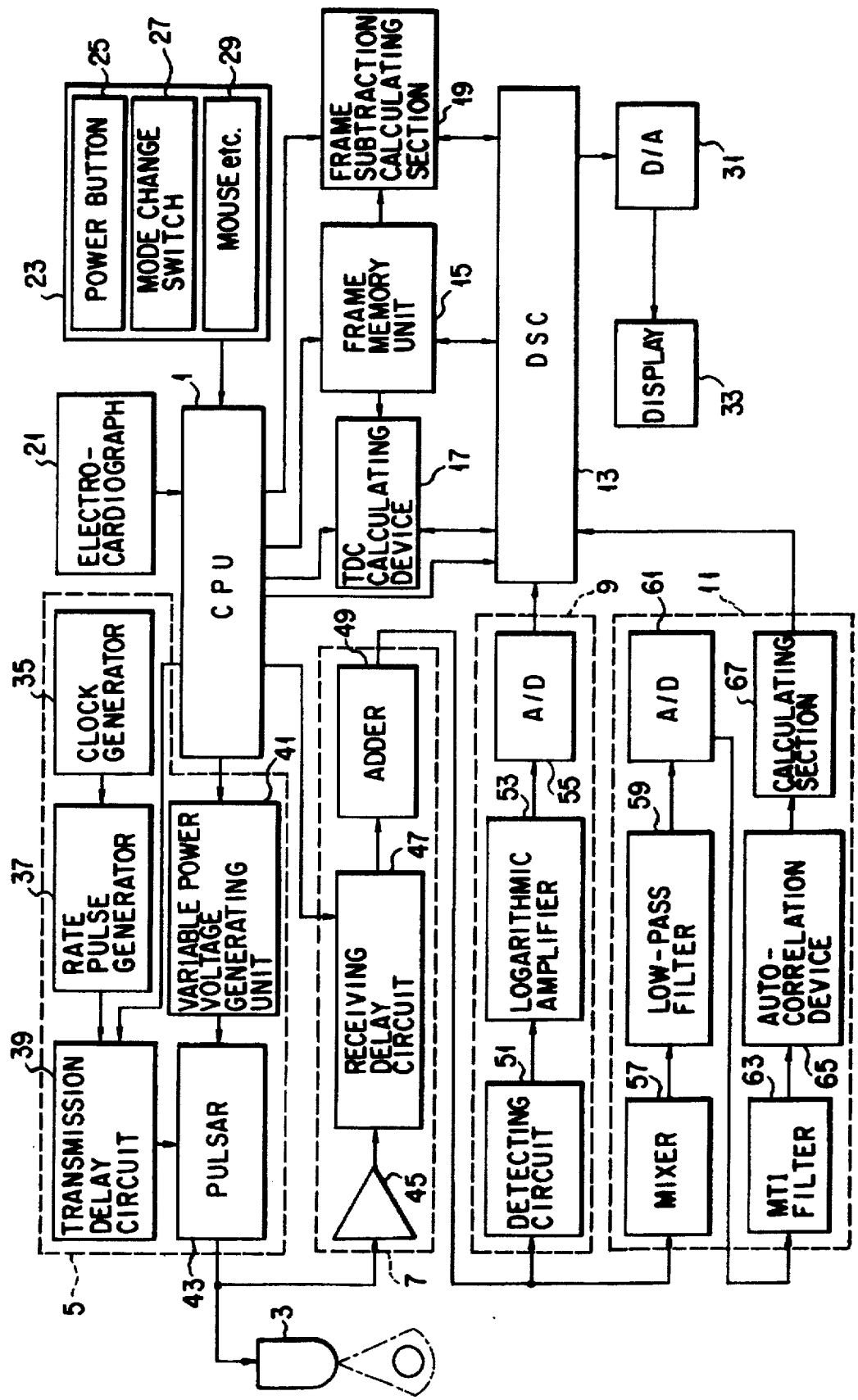
F I G. 1

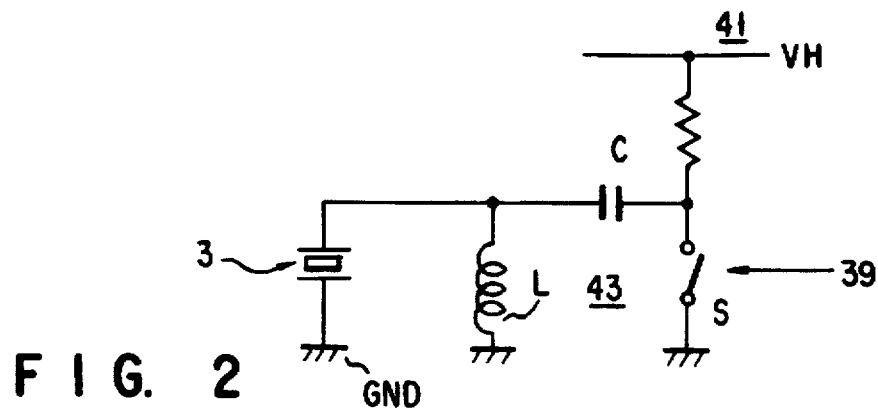
F I G. 2
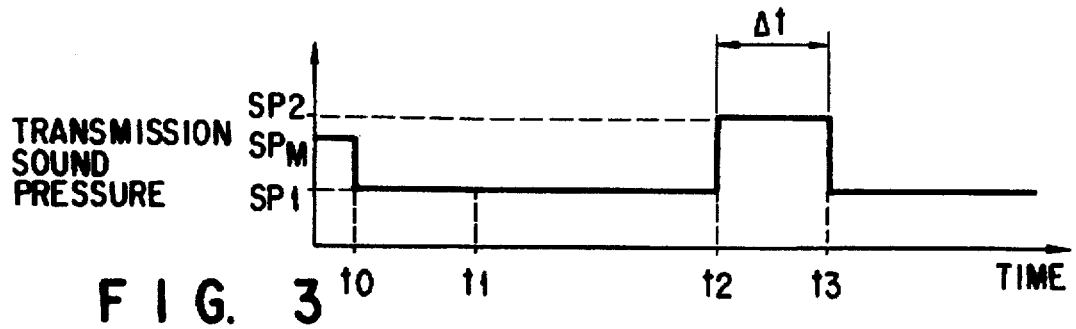
F I G. 3
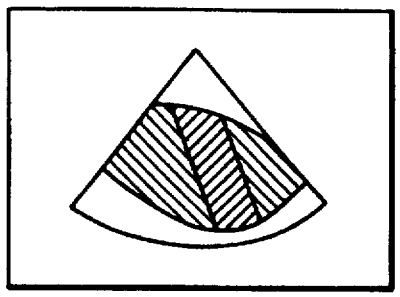
F I G. 4A
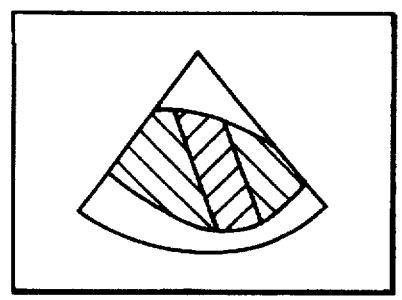
F I G. 4B
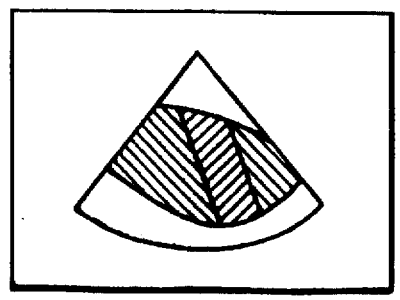
F I G. 4C

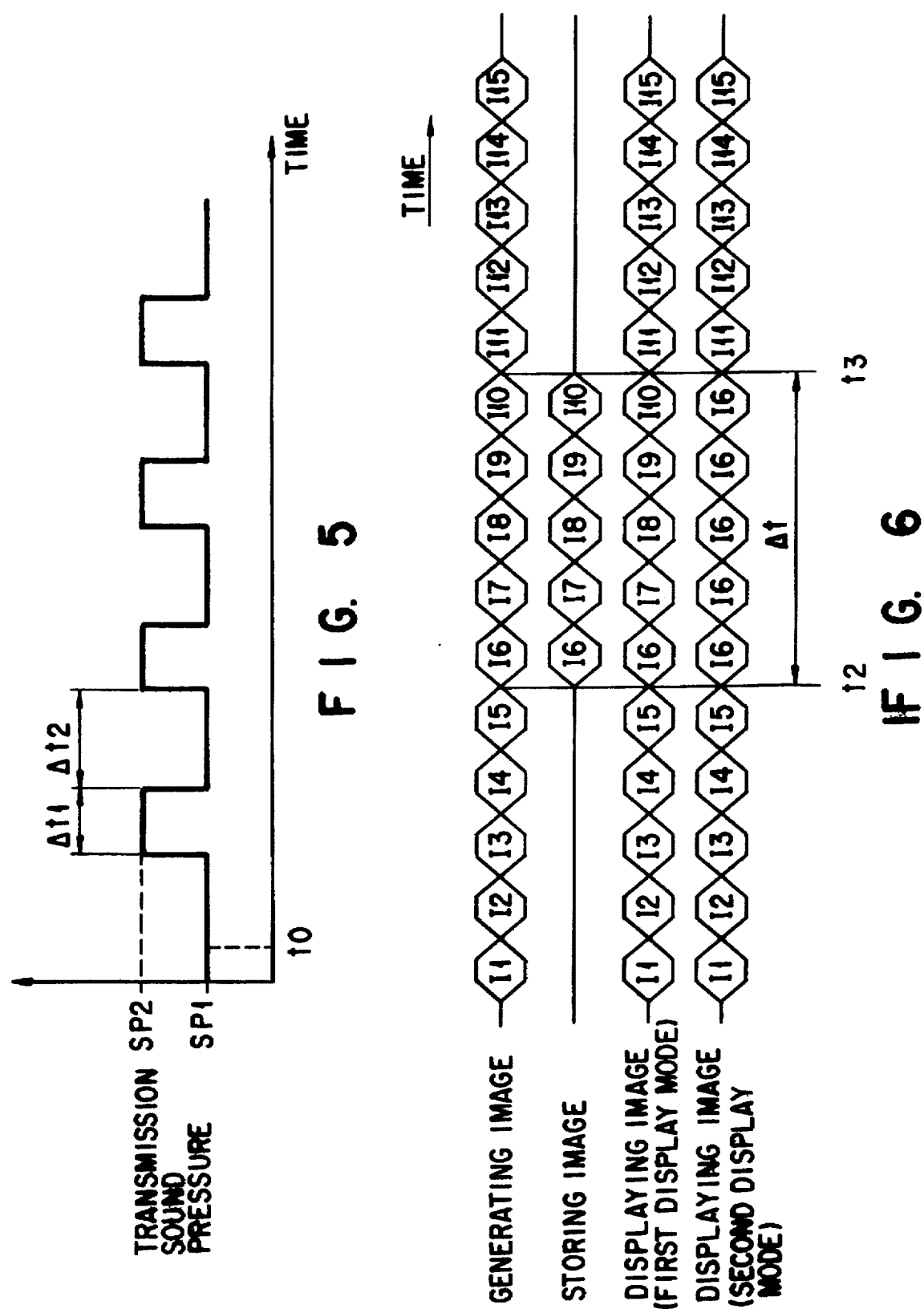

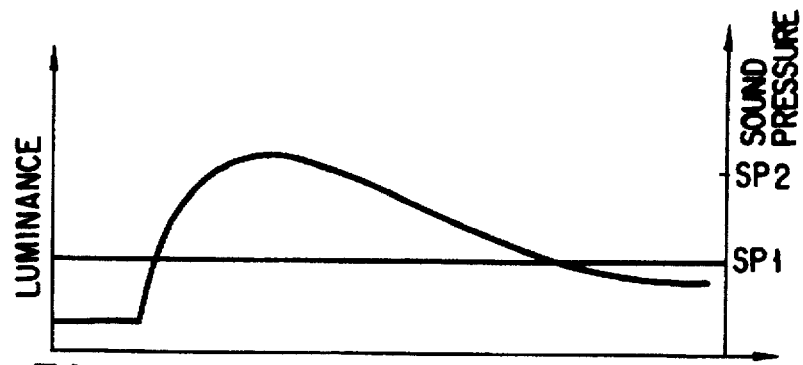
F I G. 7A
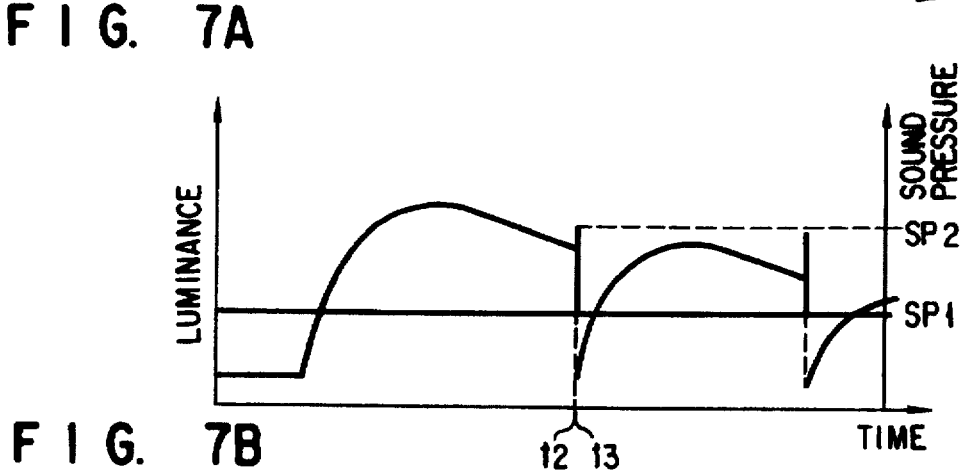
F I G. 7B
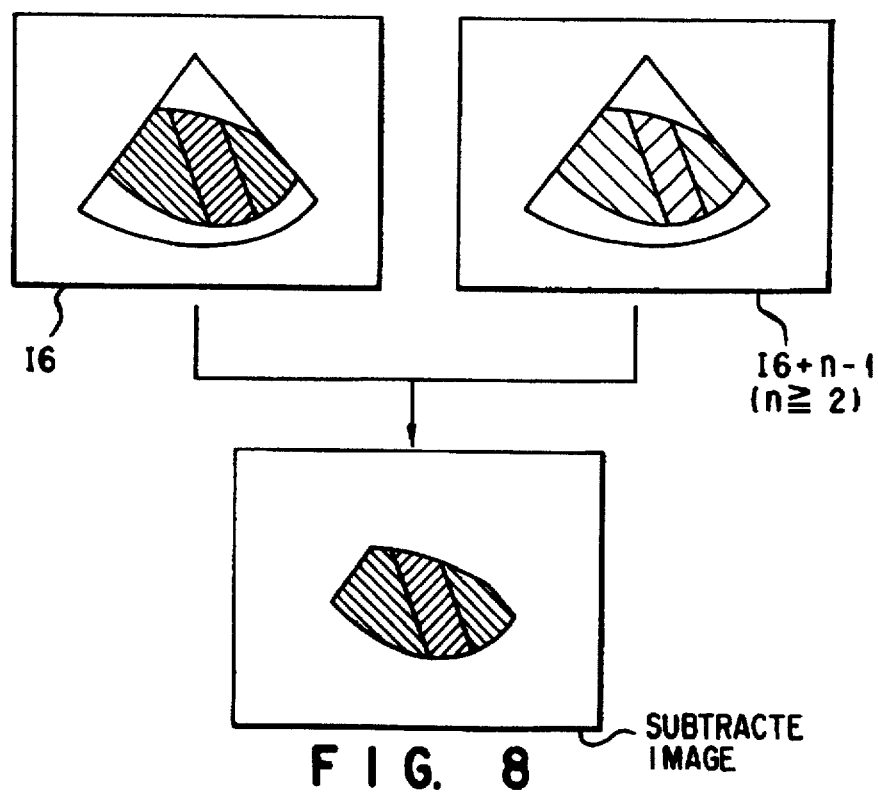
F I G. 8

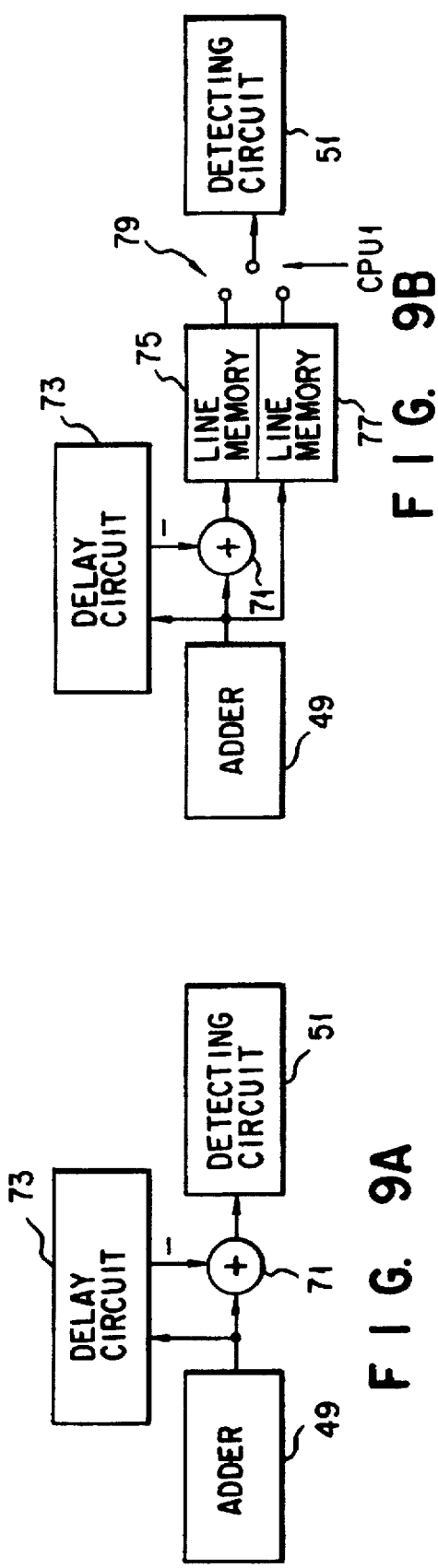
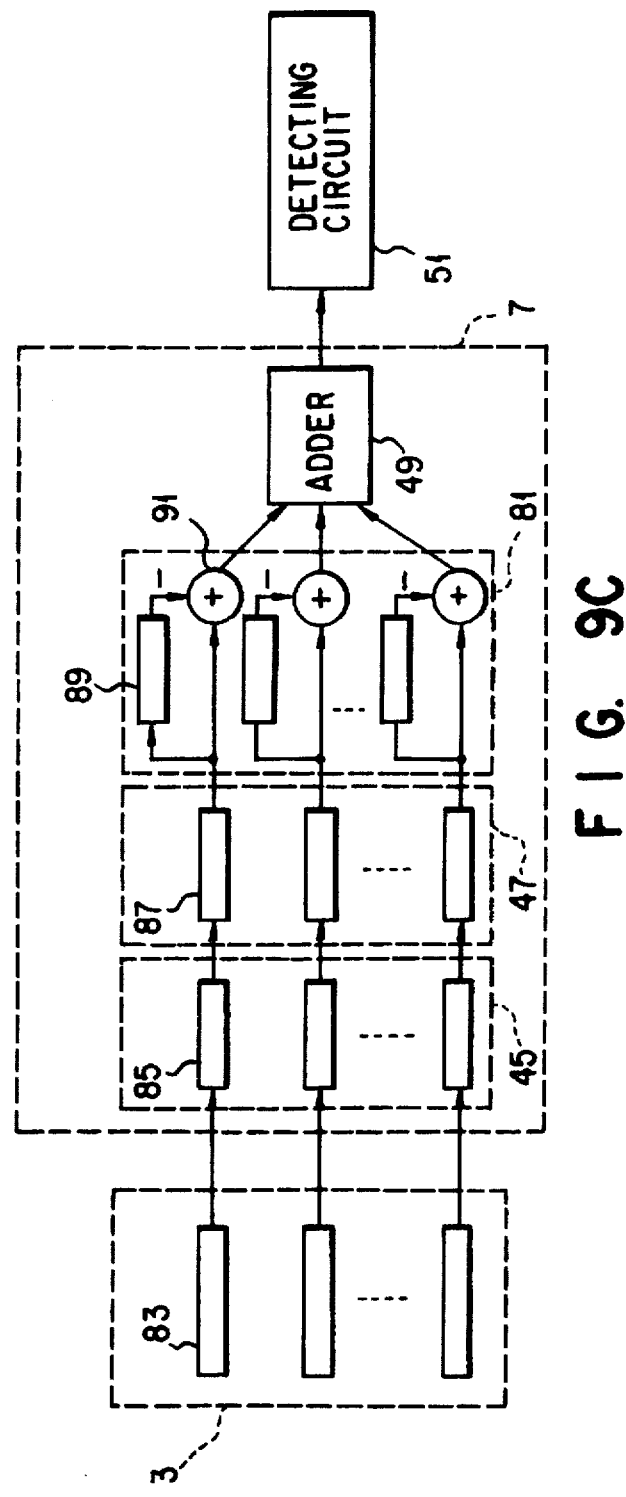
FIG. 9A
FIG. 9B
FIG. 9C

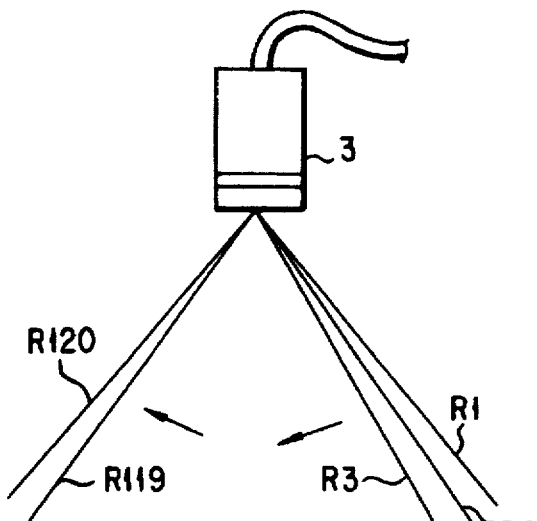
F I G. 10A
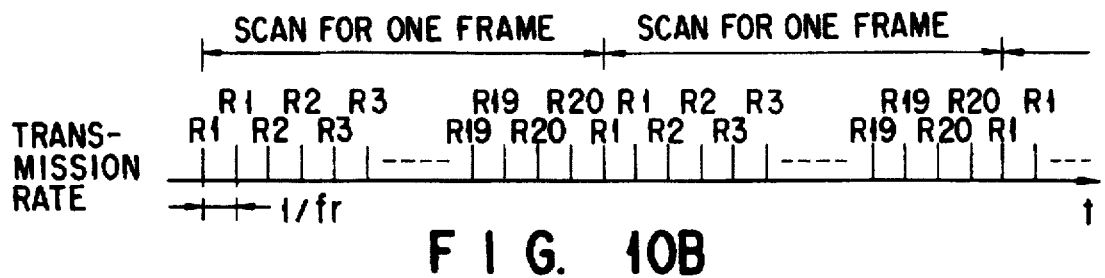
F I G. 10B
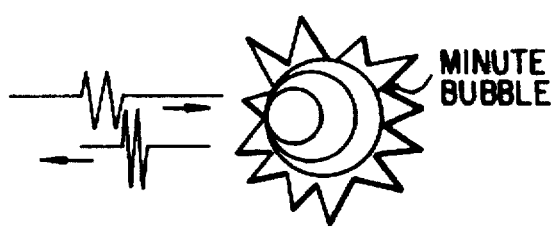
F I G. 10C
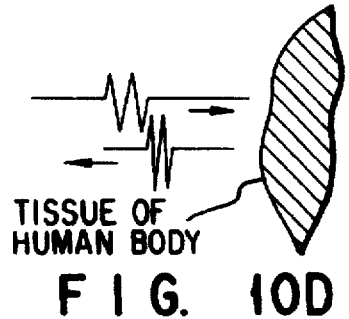
F I G. 10D
F I G. 10E
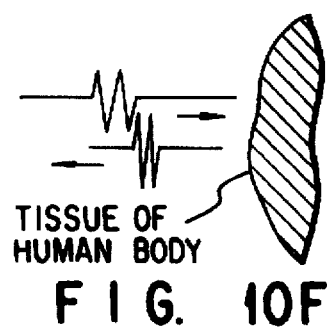
F I G. 10F

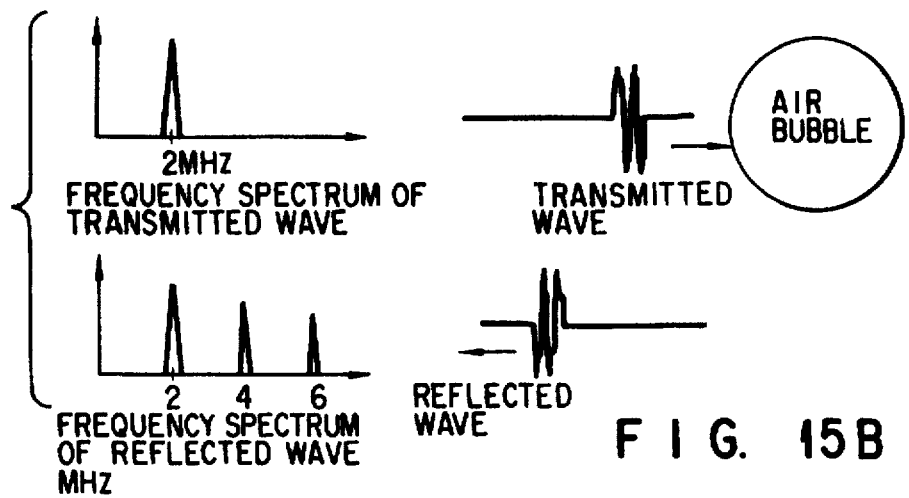
F I G. 15B
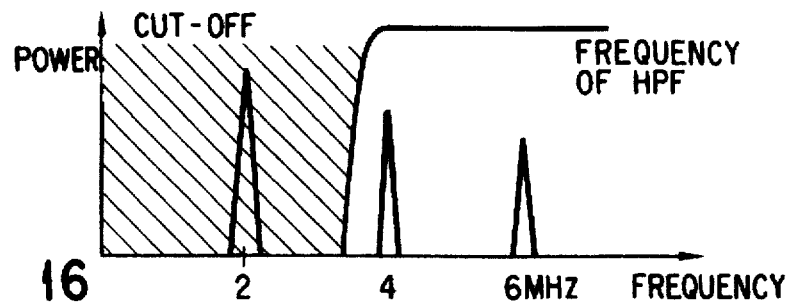
F I G. 16
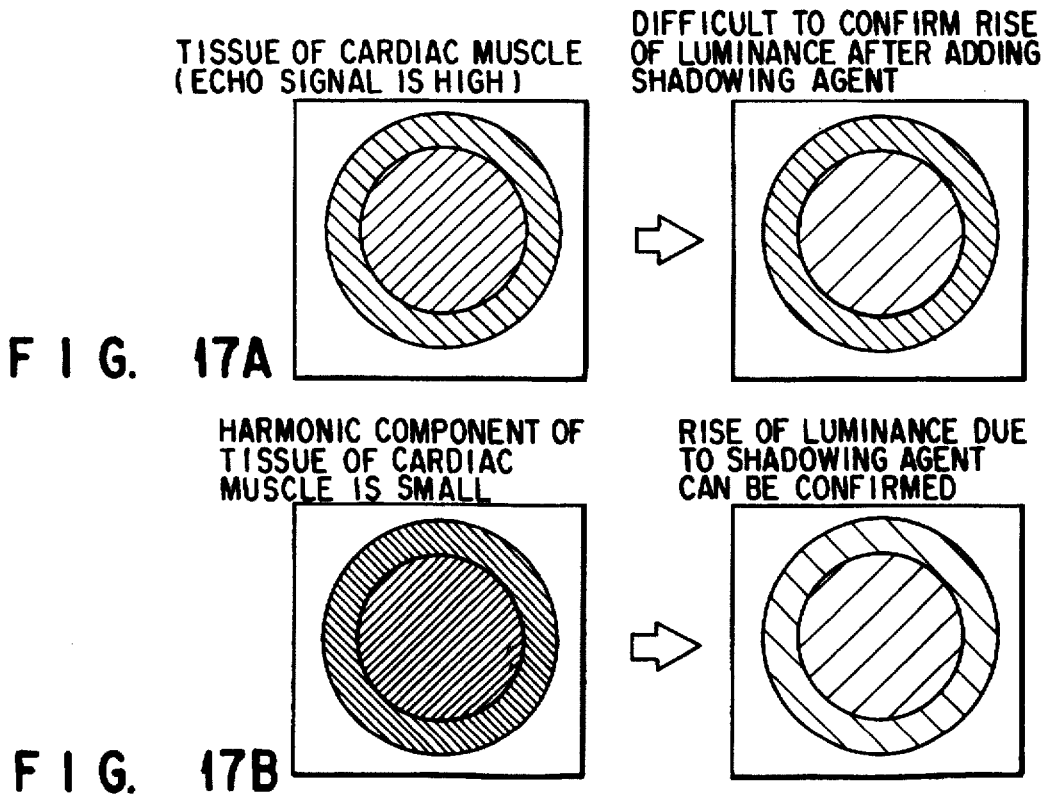
F I G. 17A
F I G. 17B

ULTRASOUND DIAGNOSTIC APPARATUS AND METHOD

BACKGROUND OF THE INVENTION

1. Field of the Invention

The present invention relates to an ultrasound diagnostic apparatus for implanting shadowing agent to an examining object so as to examine a blood stream state, and its method.

2. Description of the Related Art

Various kinds of apparatus have been used as a medical application of ultrasound. Particularly, there has been mainly used an ultrasound diagnostic apparatus for obtaining a tomographic image of a soft tissue of a human body by an ultrasonic pulse reflection method. This kind of the ultrasound diagnostic apparatus displays the tomographic image of the tissue in a non-harmful examination method. This kind of the ultrasound diagnostic apparatus has the following features as compared with the other apparatus such as an X-ray diagnostic apparatus, an X-ray CT apparatus, an MRI apparatus (magnetic resonance image apparatus) and other medical diagnostic apparatus.

More specifically, a real time display can be performed; the apparatus is small-sized, and the manufacturing cost is low, and the safety of using the apparatus is high, i.e., no suffering from X ray.

Due to this, ultrasound diagnosis has been widely performed in the examination of the heart, the abdomen, the mammary gland, the urinary organs, and the obstetrics and gynecology. Particularly, the beat of the heart and the state of the movement of an embryo can be display at real time by the simple operation in which an ultrasonic probe is only touched on a surface of the body. Moreover, the examination is repeatedly performed due to high safety, and the examination when the apparatus is moved to the head side can be easily performed. Furthermore, the technique for image-forming the blood stream, which is called as a color-doppler method, is peculiar to the ultrasound diagnosis. However, in the color-doppler method, a relatively thick blood vessel can be image-formed, but the examination of a capillary cannot be performed.

In order to solve the above problem, attention has been recently paid to a contrast echo method using ultrasonic shadowing agent. In the contrast echo method, intensity of reflection from the blood stream is increased, thereby making it possible to clearly image-form the blood vessels including from a relatively thick trunk blood vessel to the capillary. As ultrasonic shadowing agent, minute bubbles have mainly used.

As diagnostic data obtained by the contrast echo method, there are a time series change of a spatial distribution of a shadow portion, time from when the shadowing agent is implanted till the agent reaches a reason of interest (ROI), a time density curve (TDC) of luminance, and maximum luminance.

The following will explain the principle of the shadowing effect briefly.

The bubbles have extremely small acoustic impedance, and the difference between the acoustic impedance of the bubbles and that of the tissue is extremely large. Therefore, intensity of reflection at a boundary between the bubbles and the tissue is extremely larger than intensity of reflection at a boundary between the tissues, so that the shadowing effect is exerted.

However, the following problem is present in the case of the bubbles.

If the bubbles receive ultrasound, the bubbles disappear by its sound pressure. The bubbles in the blood expand like a spring by vibration of the sound pressure. If the bubbles expand and contract by a resonance frequency in accordance with its diameter, amplitude of expansion and contraction shows a maximum diameter, and a reduction speed of an amount of bubbles becomes maximum.

All bubbles do not necessarily disappear at one time of receiving and transmitting ultrasound. However, by the repetition of receiving and transmitting ultrasound several times per one second, shadow agent substantially disappears instantaneously. Due to this, the shadowing effect is reflected on only the image for several frames, and it is difficult to confirm the shadowing effect on a motion image for 30 frames per second if the amount of implanted shadowing agent is small.

In order to solve the above problem, output power (sound pressure) of ultrasound may be reduced to the extent that shadowing agent does not appear for a fixed period of time. However, the reduction of output power lowers spatial resolution. Also, in order to solve this problem, concentration of shadowing agent to be implanted may be increased, or shadowing agent may be repeatedly implanted. However, in consideration of danger to the examining human body, this method is unfavorable.

In order to extend the life of the shadowing agent, it is preferable to scan the examining human body with ultrasound of low power. In this case, however, the contrast is lowered. In order to obtain an image of a high contrast, on the other hand, it is necessary to scan the examining human body with ultrasound of a high power. In this case, however, the use of the high-power ultrasound will shorten the life of the shadowing agent. In order to make the life of the shadowing agent as long as possible and, at the same time, obtain a high contrast image, it may be considered that the examining human body be scanned, only once for a few seconds, with the high-power ultrasound. This method, however, poses the problem of a lowered time resolution.

SUMMARY OF THE INVENTION

The present invention relates to an ultrasound diagnostic apparatus, which can improve efficiency of using ultrasonic shadowing agent, and its method.

According to a first aspect of the present invention, there is provided an ultrasound diagnostic apparatus comprising scanning means for repeatedly scanning a cross section of an examining human body having bubbles implanted as ultrasonic shadowing agent by an ultrasound so as to collect an echo signal; image generating means for repeatedly generating image data based on the echo signal; displaying means for displaying the generated image data as a motion image; and changing means for changing power of the ultrasound from first power to second power stronger than the first power.

According to a second aspect of the present invention, there is provided an ultrasound diagnostic apparatus comprising scanning means for repeatedly scanning a cross section of an examining human body having bubbles implanted as ultrasonic shadowing agent by an ultrasound so as to repeat an echo signal; image generating means for repeatedly generating image data based on the echo signal; displaying means for displaying the generated image data as a motion image; and changing means for changing a frequency of the ultrasound from a first frequency to a second frequency.

According to a third aspect of the present invention, there is provided an ultrasound imaging method, which repeatedly scans a cross section of an examining human body having bubbles implanted as ultrasonic shadowing agent by an ultrasound so as to obtain an echo signal, repeatedly generates image data based on the echo signal, and displays the generated image data as a motion image, comprising a first step of scanning the ultrasound by first power; and a second step of scanning the ultrasound by second power stronger than the first power after scanning the ultrasound by the first power.

According to a fourth aspect of the present invention, there is provided an ultrasound imaging method, which transmits an ultrasound to an examining human body having bubbles implanted as ultrasonic shadowing agent, receives a reflected wave from the examining human body so as to repeatedly obtain an echo signal of a cross section of the examining human body, repeatedly generates image data based on the echo signal, and displays the generated image data as a motion image, comprising a first step of scanning the ultrasound by a first frequency; and a second step of scanning the ultrasound by a second frequency after scanning the ultrasound by the first frequency.

According to the above-mentioned present invention, a cross section of an examining human body having bubbles implanted as ultrasonic shadowing agent is scanned by an ultrasound so as to obtain an echo signal. Image data is repeatedly generated based on the echo signal. Then, image data is displayed as a motion image. Power of the ultrasound to be transmitted is changed from first power to second power, which is stronger than first power. The ultrasound of first power breaks a first amount of bubbles. The ultrasound of second power, which is stronger than first power, breaks a second amount of bubbles, which is larger than the first amount of bubbles. Though the image generated by use of first power is unclear, the amount of breakage of bubbles can be extremely retrained. Since the image is used to examine the state of the bubble flow to the region of interest, unclearness can be allowed. When the bubbles are fully introduced to the region of interest, first power is changed to second power. Second power is stronger than first power. Therefore, the image obtained by second power is clearer than image obtained by first power, and is fit for a high accurate diagnosis of the state of the blood stream.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 1 is a structural view of an ultrasound diagnostic apparatus of a first embodiment of the present invention;

FIG. 2 is a simple circuit diagram showing an ultrasonic probe, a pulsar, and a variable voltage generating unit;

FIG. 3 is a graph showing a time series change of sound pressure of ultrasound in a first mode;

FIG. 4A is a view showing a B mode image obtained by first power;

FIGS. 4B and 4C are views showing a B mode image obtained by second power;

FIG. 5 is a graph showing a time series change of sound pressure of ultrasound in a second mode;

FIG. 6 is a time chart showing processing steps of generation of image data, a storage, and a display;

FIG. 7A is a graph showing a first time series change of sound pressure of ultrasound, and a time density curve corresponding to the time series change;

FIG. 7B is a graph showing a second time series change of sound pressure of ultrasound, and a time density curve corresponding to the time series change;

FIG. 8 is an explanatory view showing a subtraction (differential) processing by a frame subtraction calculating section 19 of FIG. 1;

FIG. 9A is a structural view of a first subtraction (differential) circuit having the same function as the frame subtraction calculating section 19;

FIG. 9B is a view showing an application of FIG. 9A;

FIG. 9C is a structural view of a second subtraction (differential) circuit having the same function as the frame subtraction calculating section 19;

FIGS. 10A to 10F are explanatory views showing scanning steps corresponding to first and second subtraction circuits;

FIG. 15B is a view showing the change of a frequency spectrum due to reflection on bubbles;

FIG. 16 is a view showing the change of a frequency spectrum of a bypass filter of FIG. 14; and FIGS. 17A and 17B are views each showing an image difference between a case that no filter is provided and a case that the filter is provided.

DETAILED DESCRIPTION OF THE PREFERRED EMBODIMENTS

Figure 11:
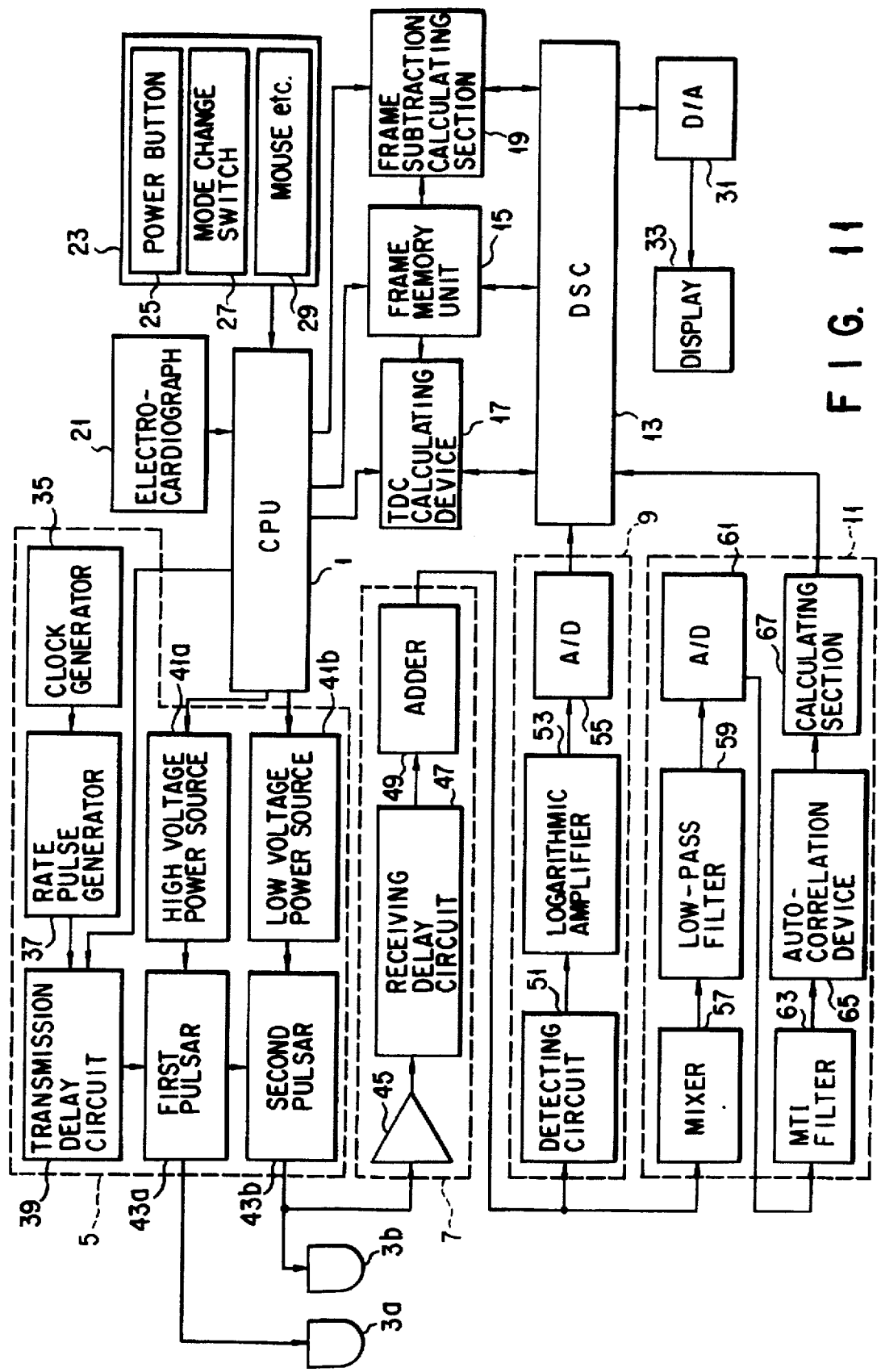
FIG. 11 is a structural view showing a modification of the ultrasound diagnostic apparatus of the first embodiment of the present invention.

The ultrasound diagnostic apparatus of the present invention is applied to an ultrasound shadowing method for examining a flood flow state at high accuracy. In the ultrasound shadowing method, ultrasonic shadowing agent is implanted to the blood of an examining human body. Levovist™ is used as ultrasonic shadowing agent. Levovist™ has minute bubbles as a main component. Acoustic impedance of bubbles is considerably low as compared with that of the tissue. Intensity of reflection at a boundary between the bubbles and the tissue is extremely larger than intensity of reflection at a boundary between the tissues. Therefore, the distribution of the bubbles is clearly expressed on an image as a distribution of the blood.

FIG. 1 is a block diagram of an ultrasound diagnostic apparatus of a first embodiment of the present invention. As an ultrasound probe 3, a sector-scan type, a linear-scan type, or the other type may be used. The ultrasound probe 3 has a piezoelectric element array at its top end. The ultrasound probe 3 is divided to a plurality of channels. For convenience, one piezoelectric element corresponds one channel.

A transmission system 5 includes a clock generator 35, a rate pulse generator 37, a transmission delay circuit 39, a variable voltage generating unit 41, and a pulsar 43. The clock generator 35 generates a clock pulse. The rate pulse generator 37 divides the clock pulse, and generates a rate pulse of, e.g., 5 KHz. The rate pulse, serving as a trigger signal, is transmitted to the pulsar 43 through the transmission delay circuit 39. The transmission delay circuit 39 distributes the rate pulse to correspond to the number of channels, and provides necessary delay time to each rate pulse so as to focus the ultrasound in a beam shape, and oscillate the ultrasound beam. The variable voltage generating unit 41 variably generates high voltage. The voltage generated by the voltage generating unit 41 is adjusted by a CPU 1. As shown in FIG. 2, the pulsar 43 includes a resonance circuit, which comprises capacitance C and inductance L, and a switch S. If the switch S is turned on by the rate pulse sent from the transmission delay circuit 39, the high voltage, which is generated by the variable voltage generating unit 41, is converted to a high frequency by the resonance circuit to be supplied to the piezoelectric element.

The ultrasound radiated to the examining human body from the ultrasound probe 3 is reflected on the boundary of the acoustic impedance. The reflected wave is received at the ultrasound probe 3, and converted to an electrical signal. The electrical signal is transmitted to a receiving system 7.

The receiving system 7 includes an amplifier 45, a receiving delay circuit 47, and an adder 49. The electrical signal sent from the ultrasound probe 3 is transmitted to the adder 49 through the amplifier 45, and the receiving delay circuit 47 every channel. The receiving delay circuit 47 provides delay time, which is reserve to time at the time of transmission, to the electrical signal. The adder 49 adds electrical signals of all channels. Thereby, an echo signal whose direction component is emphasized in accordance with delay time is generated.

A B mode processing system 9 includes a detecting circuit 51, a logarithmic amplifier 53, and an analog-digital converter (A/D) 55.

The detecting circuit 51 detects an envelop of the echo signal sent from the adder 49. The logarithmic amplifier 53 logarithmically amplifies the detected signal. The analog-digital converter 55 converts the logarithmically amplified signal to a digital signal. This digital signal is called as original data of a B mode image. The original data of the B mode image is sent to a display 33 through a digital-analog converter (D/A) 31, and its variable density is displayed.

A color flow mapping processing system 11 includes a mixer 57, a low pass filter 59, an analog-digital converter 61, an MTI filter 63, an auto-correlation device 65, and a calculating section 67. The mixer 57 and the low pass filter 59 form an orthogonal phase detecting circuit. The orthogonal phase detecting circuit extracts a deviation frequency component due to Doppler effect from the echo signal. The signal of the deviation frequency component is converted to a digital signal by the analog-digital converter 61. The MTI filter 63 removes a crack component, and extract only a blood stream component having high moving speed from the signal of the deviation frequency component sent from the analog-digital converter 61. The calculation section 67 generates a blood stream image based on the deviation frequency of the blood stream component. The blood stream image is a spatial distribution of blood speed, that of speed dispersion, or that of power. The digital signal of the blood stream image is called as original data of the blood stream image. Original data of the blood stream image is sent to a digital scan converter 13. The digital scan converter 13 suitably interpolates original data of the blood stream image, and generates blood stream image data by scanning conversion. Blood flow image data is sent to a display 33 through the digital-analog converter (D/A) 31 so as to be color-displayed.

A frame memory unit 15, a TDC calculation section 17, and a frame subtraction calculation section 19 are connected to the digital scan converter 13. The frame memory unit 15 stores image data corresponding to a plurality of frames generated by the digital scan converter 13. In this case, any one of B mode image data and blood stream image data may be used. The following will explain the case of B mode image data.

More specifically, writing and reading of image data to/from the frame memory unit 15 is controlled by CPU 1. The TDC calculation section 17 generates a time density curve of luminance (pixel value) of image data based on image data, which is directly supplied from the digital scan converter 13 or indirectly supplied through the frame memory unit 15. The time density curve shows time series change of reflection density of the reflected wave. Image data used in generating time density carve data is selected by the CPU 1. The time density curve is sent to the display 33 through the digital-analog converter 31 to be displayed as a time density curve. The frame subtraction calculation section 19 subtracts image data corresponding to two frames, which is directly supplied from the digital scan converter 13 or indirectly supplied through the frame memory unit 15. Thereby, subtraction image data is generated. Differential image data shows a spatial distribution of the time serial change of luminance. Image data, corresponding two frames, used in generating subtraction image data is selected by the CPU 1.

An electro-cardiograph 21 and a console 23 are connected to the CPU 1. The electro-cardiograph 21 detects an electrocardiographic wave of the examining human body. The console 23 includes a power button 25 for indicating that power of ultrasound transmitted from the probe 3 is changed from lower power to low power, a mode change switch 27, a mouse 29 for setting region of interest, and a keyboard for inputting various conditions.

The following will explain an operation of the embodiment of the present invention. In this case, power of ultrasound is defined in a form that sound pressure of the ultrasound is time-integrated. By enhancing amplitude of the voltage applied to the probe or increasing the number of pulse waves, power of the ultrasound is increased.

(First Mode)

FIG. 3 shows a time series change of sound pressure of ultrasound in the first mode. Bubbles are implanted to the examining human body at time $t_1$. Until the power button 25 is pressed at time $t_2$, a first control signal is supplied to the variable voltage generating unit 41 from the CPU 1. For the period of time, which is from time $t_2$ when the power button 25 is pressed to predetermined time $\Delta t$, a second control signal is supplied to the variable voltage generating unit 41 from the CPU 1. The length of predetermined time $\Delta t$ can be freely controlled by use of the console 23 by an operator. After time $t_3$ when predetermined time $\Delta t$ is passed since time $t_2$, the control signal to be supplied to the variable voltage generating unit 41 from the CPU 1 is automatically returned to the first control signal.

When the first control signal is supplied to the variable voltage generating unit 41 from the CPU 1, the variable unit 41 generates a first voltage. When the second control signal is supplied to the variable voltage generating unit 41 from the CPU 1, the variable unit 41 generates a second voltage, which is higher than the first voltage.

When the ultrasonic probe 3 is driven by the first voltage, the ultrasound is transmitted from the ultrasonic probe 3 by first power (first sound pressure SP1). When the ultrasonic probe 3 is driven by the second voltage, the ultrasound is transmitted from the ultrasonic probe 3 by second power (second sound pressure SP2), which is larger than the first power.

A first amount of bubbles per unit time is broken by first power. A second amount of bubbles per unit time, which is larger than the first amount, is broken by second power. The amount of bubbles broken by first power per unit time is absolutely smaller than the amount of bubbles broken by second power per unit time.

FIG. 4A shows that a first image is lower than a second image in the spatial resolution, and the obtained image is unclear. In this case, the first image means an image, which is generated based on an echo signal obtained when a signal cross section of the examining human body is scanned by first power. Then, the second image means an image, which is generated based on an echo signal obtained when a signal cross section of the examining human body is scanned by second power so as to obtain an echo signal.

FIG. 4B shows that the second image is higher than the first image in the spatial resolution, and the obtained image is clear.

Most of the bubbles are subjected to radiation of the ultrasound of second power so as to be broken for an extremely short period of time. FIG. 4C shows an image after the breakage of the bubbles.

If the operator wishes to confirm that the bubbles are fully introduced to the region of interest as motoring the unclear image, the operator pushes the power button 25. Thereby, there can obtained an clear image for at least one frame by which high accurate diagnosis can be expected.

Though the image generated by use of first power is unclear, the amount of breakage of bubbles can be extremely retrained. Since the image is used to examine the state of the bubble flow to the region of interest, unclearness can be allowed. When the bubbles are fully introduced to the region of interest, first power is changed to second power. Second power is stronger than first power. Therefore, the image obtained by second power is clearer than image obtained by first power, and is fit for a high accurate diagnosis of the state of the blood stream.

(Second Mode)

FIG. 5 shows a time series change of sound pressure of ultrasound in the second mode. A first period of time Δt1 when the cross section of the examining human body is scanned by the ultrasound of first power and second period of time Δt2 when the cross section of the examining human body is scanned by the ultrasound of second power are alternately repeated. In this case, no ultrasound may not be transmitted for the first period of time Δt1. The first period of time Δt1 and the second period of time Δt2 are variable. The operator can individually adjust the first period of time Δt1 and second period of time Δt2 by use of the console 23.

Most of the bubbles of the region of interest are broken at the second period of time Δt2. Then, at the next period of time Δt1, new bubbles flows into the region of interest together with the blood stream. At the next period of time Δt2, image data having clearness and high shadowing effect can be obtained.

Since the first period of time Δt1 and the second period of time Δt2 are alternately repeated, image data having clearness and high shadowing effect can be repeatedly obtained by one bubble implantation. The second period of time Δt2 may be synchronized with the electrocardiographic wave obtained from the electro-cardiograph.

FIG. 6 is a time chart showing the flow of the generation of image data, that of the storage thereof, and that of the display thereof. In this time chart, for convenience, time delay relevant to image data transfer, writing, and reading is excepted. Time t2 and t3 of FIG. 6 correspond to time t2 and t3, respectively.

If the cross section of the examining human body is repeatedly scanned by the ultrasound, image data I1, I2, I3, ... is repeatedly generated. Unclear image data I1 to I5, I11 to I15, which is generated based on the echo signal obtained when the cross section of the examining human body is scanned by first power, is not stored in the frame memory unit 15. Clear image data I6 to I10, which is generated based on the echo signal obtained when the cross section of the examining human body is scanned by second power, is stored in the frame memory unit 15. More limitedly, image data I6, which is first generated after power of the ultrasound is changed from first power to second power, is surely stored in the frame memory unit 15. Since first image data I6 is generated when second power, which is stronger than first power, is used, and the bubbles are not broken, by the ultrasound of second power, the clearest image having the highest shadowing effect can be obtained. The bubbles are sharply broken if the bubbles are subjected to the ultrasound of second power. As compared with first image data I6, the shadowing effect of image data I7, which is second generated after power of the ultrasound is changed from first power to second power, is reduced in accordance with the amount of the bubbles, which are broken by first second power.

The clearest image I6 having the highest shadowing effect is displayed as a static image of for a predetermined period of time Δt since the power button 25 is pressed. Image I6 is repeatedly read from the digital scan converter 13 at a fixed cycle. Moreover, image data I6 to I10, which is generated after the power button 25 is pressed, is displayed as a motion image. However, in the case that image data is displayed as a motion image, it is considerably difficult for the operator to capture first image data I6, in consideration of the display period per one frame, e.g., 1/30 seconds. Due to this, it is preferable that first image data I6 be displayed in the static state.

Graphic data, which shows a power state of the ultrasound prepared by the CPU 1, is synthesized with image data by the digital scan converter 13. Then, the power state of the ultrasound is displayed on the display 33 together with image data. In this case, the power state of the ultrasound is data for identifying whether the present ultrasound is transmitted by first power or second power.

Next, the following will explain the generation of time density curve data due to the TDC calculation section 17.

First, the conventional method for generating time density curve data will be explained as follows.

More specifically, the ultrasound is fixed to first power SP1 for the period of time when time density curve data is generated. Image data for the plurality of frames, which is sequentially generated, is supplied to the TDC calculation section 17 from the digital scan converter 13 or the frame memory unit 15. A pixel value (luminance) of a specific one pixel or a total value of the plurality of pixel values of the region of interest is extracted from image data of each frame, and calculated by the TDC calculation section 17. Luminance of each image data is plotted at a position where a vertical axis corresponds to a luminance value and a horizontal axis corresponds to time. As shown in FIG. 7A, data of time density curve is generated. The time density curve describes the state showing an inflow of shadowing agent to the region of interest and an outflow thereof.

The following will explain a method for generating time density curve data of the embodiment of the present invention with reference to FIG. 7B.

When time density curve data is generated, the second mode is selected by the CPU 1. In other words, the change of power from first power SP1 to second power SP2 is intermittently repeated. The second period of time $\Delta t2$ when second power SP2 is continued is automatically set to extremely short period of time, which is needed to break most of the bubbles of the region of interest, by the CPU 1. If the ultrasound is transmitted by second power SP2, the most of the bubbles of the region of interest are broken. After the most of the bubbles are broken, new bubbles flow to the region of interest together with the blood stream. The change of power from first power SP1 to second power SP2 is intermittently repeated. Thereby, the bubbles of the region of interest substantially disappear. Then, new bubbles repeatedly flow to the region of interest. The state sowing the inflow of shadowing agent to the region of interest and the outflow thereof can be repeatedly described by one density curve.

Time density curve data generated by the TDC calculation section 17 is displayed on the display 33 as a time density curve showing time series change of luminance through the digital scan converter 13, and the digital-analog converter 31.

The ultrasound of second power SP2 is transmitted only to break the bubbles. Due to this, the ultrasound may be transmitted to scan not only the cross section of the examining human body but also a relatively wide three-dimensional region including the cross section of the examining human body. In this case, the ultrasonic probe 3 in which the plurality of piezoelectric elements are two-dimensionally arrayed is used. The delay control due to the transmission delay circuit 39 is changed so as to scan the three-dimensional region. Or, the scanning of the three-dimensional region is achieved by changing the delay control due to the transmission delay circuit 39 such that the ultrasound is not focused by the CPU 1, that is, the ultrasound is dispersed. In the latter case, it is unnecessary to replace the probe in which the piezoelectric elements are one-dimensionally arrayed with the ultrasonic probe in which the piezoelectric elements are two-dimensionally arrayed.

The following will explain the subtraction processing of the embodiment of the present invention with reference to FIG. 8. In this case, it is assumed that the first mode of FIG. 3 is executed.

Image data for two fames, that is, image data I6, which is first generated after power of the ultrasound is changed from first power to second power, and image data I6+n−1, which is nth generated in a state that second power is maintained, is supplied to the frame subtraction calculating section 19 from the digital scan converter 13 or the frame memory unit 15. In this case, n is $10 \geq n \geq 2$, and is set, in advance, to a minimum number of transmissions, which is needed such that most of the bubbles are broken by the ultrasound of second power SP2.

Image data for two frames, that is, first generated image data I6 and nth generated image data I6+n−1, is subtracted from each other between the frames by the frame subtraction calculating section 19. The shadowing effect of first generated image data I6 is maximum. Then, the shadowing effect of nth generated image data I6+n−1 is lower than that of image data I6. The tissue portion is unchanged between two frames. There is generated subtraction image data in which the tissue portion is removed and only the spatial distribution of shadowing agent is extracted.

Time density curve data generated by the TDC calculation section 17 is displayed on the display 33 as a time density curve showing time series change of luminance through the digital scan converter 13, and the digital-analog converter 31.

The frame subtraction calculating section 19 can be modified as follows.

More specifically, in the modification, the scanning step for scanning the cross section of the examining human body is changed. As shown in FIG. 10A, the cross section of the examining human body is scanned by ultrasonic scanning lines R1, R2, ... R120. As shown in FIG. 10B, the receiving and transmitting of the ultrasound is repeated twice in connection with each of the ultrasonic scanning lines R1, R2, ... R120. In FIG. 10B, fr is a rate frequency, and 1/fr shows a cycle of the receiving and transmitting of the ultrasound. As shown in FIGS. 10C and 10D, the ultrasound, which is first transmitted, is reflected on the bubble and the tissue. The bubbles are broken by the first ultrasound. As shown in FIGS. 10E and 10F, the ultrasound transmitted, which is transmitted at the second time, is reflected on only the tissue. Therefore, the echo signal, which is obtained at the first receiving and transmitting, includes the bubble component and the tissue component. The echo signal, which is obtained at the second receiving and transmitting, includes only the tissue component.

As shown in FIG. 9A, an adder 71 and a delay circuit 73, serving as a subtraction circuit, are provided between the adder 49 of the receiving system 7 and the detecting circuit 51 of the B mode processing system 9. The delay circuit 73 provides delay time of 1/fr to the echo signal sent from the adder 49. The echo signal, which is obtained at the first receiving and transmitting, and the echo signal, which is obtained at the second receiving and transmitting, are synchronized with each other to be supplied to the delay circuit 73. If these two echo signals are subtracted from each other by the adder 71, the tissue component is removed, and only the bubble component remains. By processing the echo signal in which the tissue component is removed and only the bubble remains, the B mode processing system 9 generates subtraction image data in which only the spatial distribution of shadowing agent is extracted. A subtraction circuit of FIG. 9B is a modification of FIG. 9A. Line memories 75 and 77, and a changer 79 are provided between the adder 71 and the detecting circuit 51, and these memories and the changer 79 are added to the subtraction circuit of FIG. 9A, thereby making it possible to select execution/ non-execution of the subtraction processing.

A subtraction circuit of FIG. 9C provides a subtraction processing to a receiving signal before being added by the adder 49. Similar to the subtraction circuit of FIG. 9A, a delay circuit 89 and an adder 91 are provided between a delay line 89, which is provided every channel, and the adder 49. The delay circuit 89 provides delay time of 1/fr to the receiving signal sent from the delay line 87. The adder 91 is used to subtract the receiving signal, which is obtained at the first receiving and transmitting, and the receiving signal, which is obtained at the second receiving and transmitting, from each other. The receiving signal, which is obtained at the first receiving and transmitting, and the receiving signal, which is obtained at the second receiving and transmitting, are synchronized with each other to be supplied to the adder 91. If these two receiving signals are subtracted from each other by the adder 91, the tissue component is removed, and only the bubble component remains. By adding only the receiving signal in which the tissue component is removed and only the bubble component remains, the adder 49 obtains an echo signal in which the tissue component is removed and only the bubble component remains. By processing the echo signal in which the tissue component is removed and only the bubble remains, the B mode processing system 9 generates subtraction image data in which only the spatial distribution of shadowing agent is extracted.

For the period of time when the receiving and transmitting of the ultrasound is repeated twice in connection with each of the ultrasonic scanning lines R1, R2, . . . R120, the transmission of the ultrasound may be performed for only the breakage of the bubbles.

The above-explained first embodiment can be modified as shown in FIG. 11. In the explanation of the first embodiment, the changing of the first and second voltages was performed by the variable voltage generating unit 41. This operation may be separated to a high voltage source 41a for generating the second voltage and a low voltage source 41b for generating the first voltage. Moreover, the pulsar 43 may be separated to a first pulsar 43a corresponding to the high voltage source 41a and a second pulsar 43b corresponding to the low voltage power source 41b. Furthermore, the ultrasonic probe 3 may be separated to a first ultrasonic probe 3a for the breakage of bubbles, which corresponds to the high voltage source 41a, and a second ultrasonic probe 3b for imaging, which corresponds to the low voltage source 41b.

(Second Embodiment)

Figure 12:
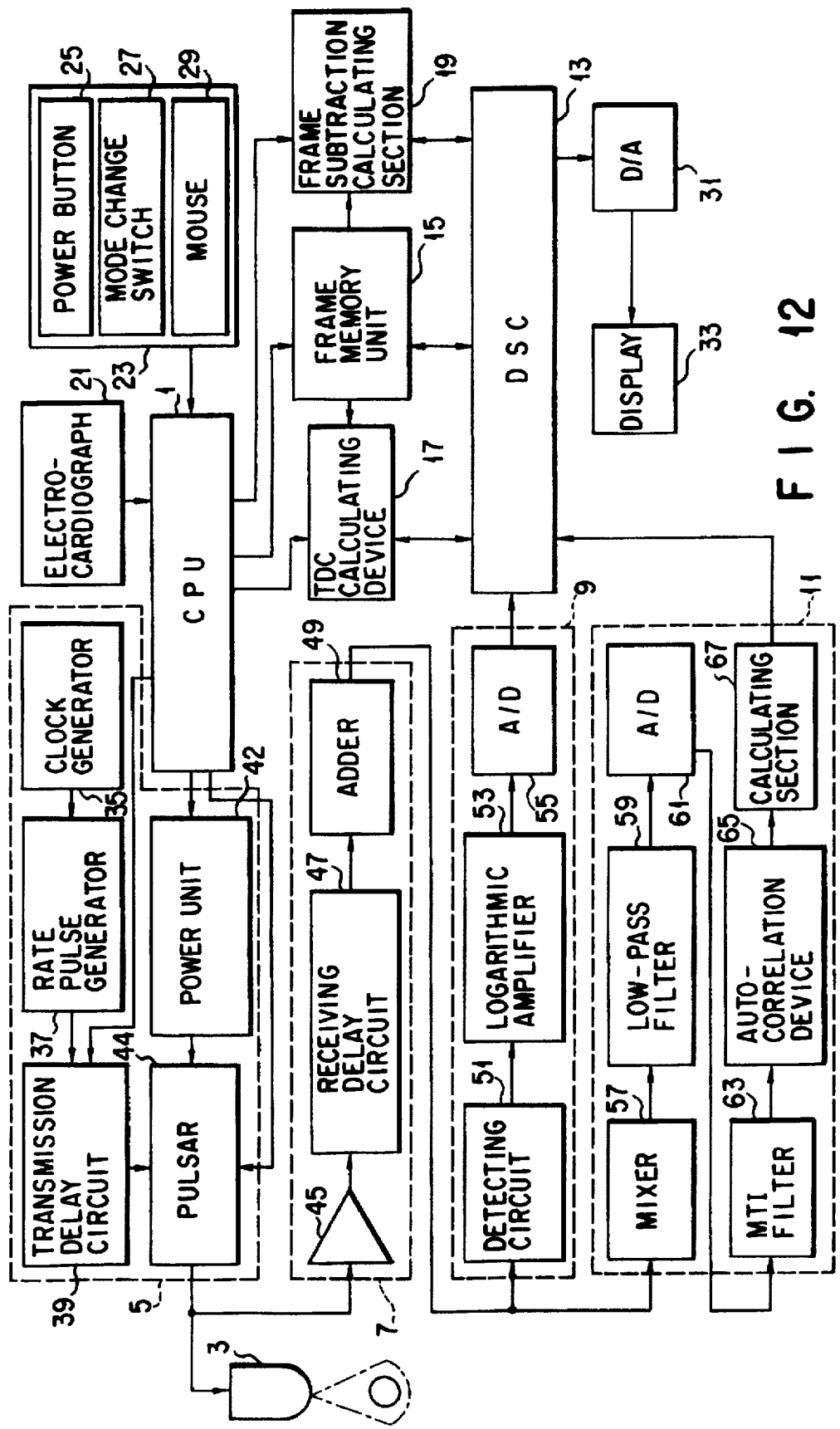
FIG. 12 is a structural view of an ultrasound diagnostic apparatus of a second embodiment of the present invention.

FIG. 12 is a structural view of an ultrasound diagnostic apparatus of a second embodiment of the present invention. In FIG. 12, the same reference numerals as FIG. 1 are added to the portions common to FIG. 1. In the first embodiment, power of the ultrasound was changed from first low power to second high power. In the second embodiment, a central frequency of the ultrasound is changed from a first frequency to a second frequency. The power source unit 42 generates a fixed voltage. In the second embodiment, power of the ultrasound is constant. A variable capacitor is used as a capacitor C of a resonance circuit of a pulse sequencer 44. The CPU 1 sets the variable capacitor to a first capacity for the period of time when the cross section of the examining human body is scanned by ultrasound of first power in the first embodiment. Thereby, an ultrasound is generated at a first central frequency from the ultrasonic probe 3. Also, the CPU 1 sets the variable capacitor to a second capacity for the period of time when the cross section of the examining human body is scanned by ultrasound of second power in the first embodiment. Thereby, an ultrasound is generated at a second central frequency from the ultrasonic probe 3.

Figure 13A:
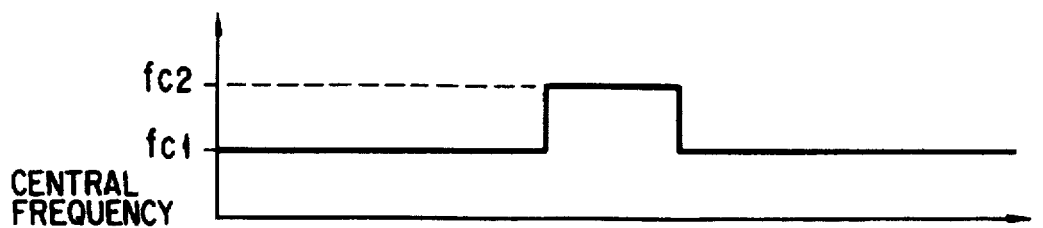
FIGS. 13A and 13B are graphs each showing a time series change of a central frequency of ultrasound.

FIG. 13A is a view showing a time series change of a central frequency of ultrasound in connection with FIG. 3.

Figure 13B:
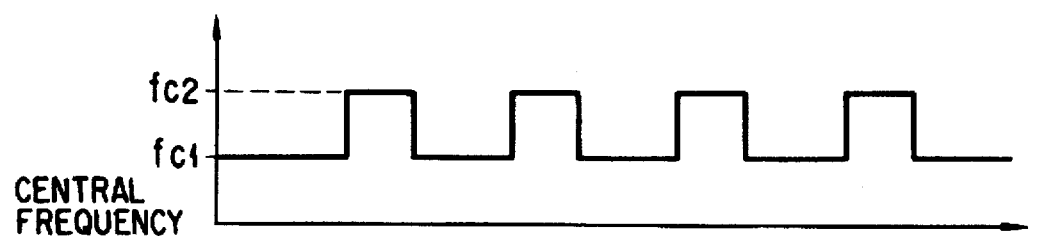

FIG. 13B is a view showing a time series change of a central frequency of ultrasound in connection with FIG. 5.

The bubbles in the blood contract/expand like a spring by vibration of sound pressure of the ultrasound. Each of the bubbles has a peculiar resonance frequency in accordance with its diameter. When the bubble contracts/expands by the peculiar resonance frequency, its amplitude shows a maximum diameter, and the breakage of the bubble advances most. The diameter of the bubble, which is actually implanted to the examining human body, is not fixed.

When the ultrasound of the first central frequency is transmitted, most of the bubbles each having a diameter corresponding to the resonance frequency, which is the same as the first central frequency, are broken. Then, most of the bubbles each having a diameter corresponding to the resonance frequency, which is other than the first central frequency, are not broken.

When the ultrasound of the second central frequency is transmitted, most of the bubbles each having a diameter corresponding to the resonance frequency, which is the same as the second central frequency, are broken. Then, most of the bubbles each having a diameter corresponding to the resonance frequency, which is other than the second central frequency, are not broken.

In other words, when the cross section of the examining human body is scanned by the ultrasound of the first central frequency to observe the inflow of the bubbles to the region of interest, most of the bubbles each having a diameter corresponding to the resonance frequency, which is the same as the first central frequency, are broken. Then, most of the bubbles each having a diameter corresponding to the resonance frequency, which is other than the first central frequency, remain without being broken.

The bubbles each having a diameter corresponding to the resonance frequency, which is other than the first central frequency, can be left until the central frequency of the ultrasound is changed from the first central frequency to the second central frequency by suitable timing. This means the same advantage as the case of the first embodiment. That is, the cross section of the examining human body is scanned by the ultrasound of the first low power, so that the breakage of the bubbles is extremely restrained.

In order to extremely restrain the amount of the breakage of the bubbles by the ultrasound of the first central frequency, it is useful to sharply narrow the band of the ultrasound. For this purpose, the voltage wave may be shaped based on a sinc function.

(Third Embodiment)

Figure 14:
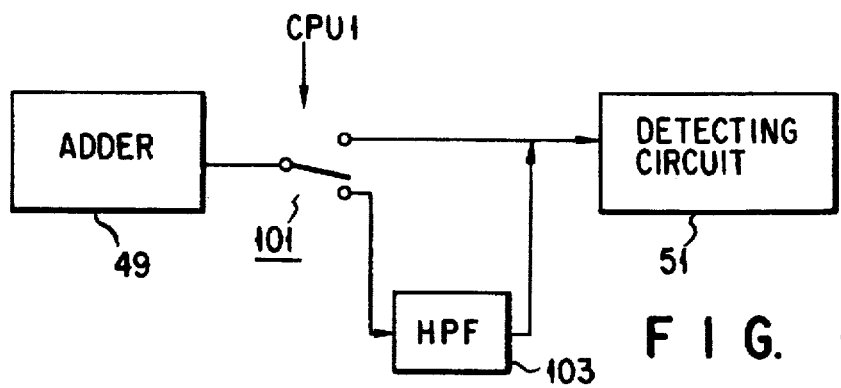
FIG. 14 is a structural view of a main part of an ultrasound diagnostic apparatus of a third embodiment of the present invention.

FIG. 14 is a structural view of a main part of an ultrasound diagnostic apparatus of a third embodiment of the present invention. The structure other than the above main part is the same as the structure of the first and second embodiments. A changer 101 and a high pass filter (HPF) 103 are provided between the adder 49 and the detecting circuit 51. The CPU 1 selectively supplies the first and second control signals. If the first control signal is supplied, the changer 101 directly connects the detecting circuit 61 to the output of the adder 49. In this case, the structure is completely the same as the structure of the first and second embodiments. If the second control signal is supplied, the changer 101 indirectly connects the detecting circuit 61 to the output of the adder 49 through the high pass filter 103. In this case, the low frequency component of the echo signal sent from the adder 49 is removed, and the high frequency component is extracted.

Figure 15A:
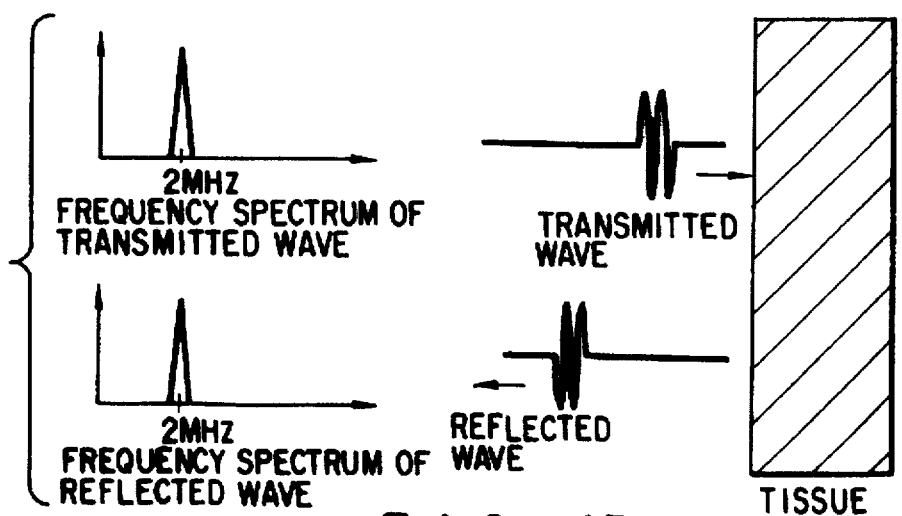
FIG. 15A is a view showing the change of a frequency spectrum due to reflection on a tissue.

FIG. 15A is a frequency spectrum of the ultrasound to be transmitted, and a frequency spectrum of a reflected wave reflected on the boundary of the tissues. The tissue substantially unchanges the frequency spectrum between the transmitted wave and the reflected wave.

FIG. 15B is a frequency spectrum of the ultrasound to be transmitted, and a frequency spectrum of a reflected wave reflected on the boundary between the bubble and the tissue. Elasticity of the bubbles substantially changes the frequency spectrum between the transmitted wave and the reflected wave. For example, if the ultrasound is transmitted by the central frequency of 2 MHz, the high frequency component of 4 MH or 6 MHz is mixed to the frequency spectrum of the reflected wave.

FIG. 16 shows a frequency characteristic of the high pass filter 103. A cutoff frequency of the high pass filter 103 is set so as to pass the high frequency component, which is not included in the reflected wave of the tissue but included in only the reflected wave of the bubbles. Also, the cutoff frequency of the high pass filter 103 is set not to pass the low frequency component, which is included in both the reflected wave of the tissue and the reflected wave of the bubbles. The high frequency component of the echo signal passed through the high pass filter 103, thereby generating image data for mainly describing the spatial distribution of shadowing agent.

As shown in FIGS. 17A and 17B, according to the third embodiment, the shadowing effect can be clearly confirmed.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An ultrasound diagnostic apparatus comprising:
    scanning means for repeatedly scanning a cross section of an examining human body having implanted bubbles as an ultrasonic shadowing agent with an ultrasound to collect an echo signal;
    image data obtaining means for repeatedly obtaining image data based on said echo signal;
    displaying means for displaying said obtained image data as a motion image;
    changing means for changing power of said ultrasound from first power to second power stronger than said first power; and
    storing means for selectively storing the image data obtained from the obtaining means during a time period in which the cross section of the examining body is scanned with the ultrasound of the second power.

2. The apparatus according to claim 1, wherein said power is sound pressure.

3. The apparatus according to claim 1, wherein said scanning means includes a piezoelectric element group and voltage generating means for variably generating a voltage for driving said piezoelectric element group, and said changing means changes the voltage generated by said voltage generating means from a first voltage corresponding to said first power to a second voltage corresponding to said second power and being higher than said first voltage.

4. The apparatus according to claim 1, wherein said image data obtain means includes means for storing image data first obtained after said power of the ultrasound is changed from said first power to said second power.

5. The apparatus according to claim 1, wherein said displaying means includes means for displaying image data first obtained after said power of the ultrasound is changed from said first power to said second power as a static image.

6. The apparatus according to claim 1, further comprising inputting means for manually designating a change of power from said first power to said second power.

7. The apparatus according to claim 1, wherein said changing means includes means for returning power of said ultrasound to said first power after the scanning is continued for a predetermined period of time by said second power.

8. The apparatus according to claim 1, wherein said image data obtaining means includes means for subtracting image data, first obtained after said power of the ultrasound is changed from said first power to said second power, and image data, nth obtained after said power of the ultrasound is changed from said first power to said second power, from each other between frames.

9. The apparatus according to claim 1, wherein said scanning means scans plural ultrasonic scanning lines and includes means for repeating a receiving and transmitting operation twice in connection with each of said ultrasonic scanning lines, and means for subtracting the echo signal obtained by the first receiving and transmitting operation and the echo signal obtained by the second receiving and transmitting operation from each other, and said image data obtaining means obtains image data based on said subtracted echo signal.

10. The apparatus according to claim 1, wherein said scanning means includes means for extracting a high frequency component from said echo signal, and said image data obtaining means obtains image data based on said high frequency component.

11. The apparatus according to claim 1, wherein said displaying means includes means for displaying a power state of said ultrasound.

12. The apparatus according to claim 1, wherein said image obtaining means includes means for obtaining a time density curve of a pixel value of said image data.

13. The apparatus according to claim 1, wherein said scanning means includes first means for generating the ultrasound by said first power, and second means for generating the ultrasound by said second power.

14. An ultrasound diagnostic apparatus comprising:
    scanning means for repeatedly scanning a cross section of an examining human body having implanted bubbles as an ultrasonic shadowing agent with an ultrasound to repeat an echo signal;
    image obtaining means for repeatedly obtaining image data based on said echo signal;
    displaying means for displaying said generated image data as a motion image;
    changing means for changing a frequency of said ultrasound from a first frequency to a second frequency; and
    storing means for selectively storing the image data obtained from the obtaining means during a time period in which the cross section of the examining human being is scanned with the ultrasound of the second frequency.

15. The apparatus according to claim 14, wherein said image obtaining means includes means for storing image data first obtained after said frequency of the ultrasound is changed from said first frequency to said second frequency.

16. The apparatus according to claim 14, wherein said displaying means includes means for displaying image data first obtained after said frequency of the ultrasound is changed from said first frequency to said second frequency as a static image.

17. The apparatus according to claim 14, further comprising inputting means for manually designating a change of the frequency from said first frequency to said second frequency.

18. The apparatus according to claim 14, wherein said changing means includes means for returning the frequency of said ultrasound to said first frequency after the scanning is continued for a predetermined period of time by said second frequency.

19. The apparatus according to claim 14, wherein said image obtaining means includes means for subtracting image data, first obtained after said frequency of the ultrasound is changed from said first frequency to said second frequency, and image data, subsequently obtained after said frequency of the ultrasound is changed from said first frequency to said second frequency, from each other between frames.

20. The apparatus according to claim 14, wherein said scanning means scans plural ultrasonic scanning lines and includes means for repeating a receiving and transmitting operation twice in connection with each of said ultrasonic scanning lines, and means for subtracting the echo signal obtained by the first receiving and transmitting operation and the echo signal obtained by the second receiving and transmitting operation from each other, and said image generating means generates image data based on said subtracted echo signal.

21. The apparatus according to claim 14, wherein said scanning means includes means for extracting a high frequency component from said echo signal, and said image data obtaining means obtains image data based on said high frequency component.

22. The apparatus according to claim 14, wherein said displaying means includes means for displaying a frequency state of said ultrasound.

23. The apparatus according to claim 14, wherein said image obtaining means includes means for obtaining a time density curve of a pixel value of said image data.

24. An ultrasound imaging method, which repeatedly scans a cross section of an examining human body having implanted bubbles as an ultrasonic shadowing agent with an ultrasound to obtain an echo signal, repeatedly obtains image data based on said echo signal, and displays said image data as a motion image, comprising:

a first step of scanning said ultrasound by first power;

a second step of scanning said ultrasound by second power stronger than said first power after scanning said ultrasound by said first power; and a third step of selectively storing the image data obtained during a time period in which the cross section of the examining human body is scanned with the ultrasound of the second power.

25. The method according to claim 24, wherein said power is sound pressure.

26. The method according to claim 25, further comprising a third step of returning power of said ultrasound to said first power after the scanning is continued for a predetermined period of time by said second power.

27. An ultrasound imaging method, which repeatedly scans a cross section of an examining human body having implanted bubbles as an ultrasonic shadowing agent with an ultrasound to obtain an echo signal, repeatedly obtains image data based on said echo signal, and displays said image data as a motion image, comprising:

a first step of scanning said ultrasound by first power;

a second step of scanning said ultrasound by second power stronger than said first power after scanning said ultrasound by said first power; and a third step of selectively storing the image data obtained during a time period in which the cross section of the examining human body is scanned with the ultrasound of the second frequency.

28. The method according to claim 27, further comprising a third step of returning the frequency of said ultrasound to said first frequency after the scanning is continued for a predetermined period of time by said second frequency.

* * * * *